US008618510B2

(12) United States Patent
Palmer et al.

(10) Patent No.: US 8,618,510 B2
(45) Date of Patent: Dec. 31, 2013

(54) OPTICALLY INTEGRATED MICROFLUIDIC CYTOMETERS FOR HIGH THROUGHPUT SCREENING OF PHOTOPHYSICAL PROPERTIES OF CELLS OR PARTICLES (75) Inventors: Amy E. Palmer, Boulder, CO (US); Ralph Jimenez, Boulder, CO (US); Kevin Dean, Lafayette, CO (US); Jennifer Lubbeck, Boulder, CO (US); Lloyd M. Davis, Tullahoma, TN (US)

(73) Assignees: The Regents of the University of Colorado, Denver, CO (US); University of Tennessee Research Foundation, Knoxville, TN (US); National Institute of Standards and Technology, Gaithersburg, MD (US)

( * ) Notice: Subject to any disclaimer, the term of this patent is extended or adjusted under 35 U.S.C. 154(b) by 0 days.

(21) Appl. No.: 13/360,706

(22) Filed: Jan. 28, 2012

(65) Prior Publication Data
US 2012/0241643 A1 Sep. 27, 2012

Related U.S. Application Data (60) Provisional application No. 61/437,562, filed on Jan. 28, 2011.

(51) Int. Cl.
*G01N 21/00* (2006.01)
*G01N 21/53* (2006.01)

(52) U.S. Cl.
USPC ........ 250/461.2; 250/251; 250/428; 356/318; 356/338; 356/400; 382/128; 382/129; 435/288.7

(58) Field of Classification Search
USPC ............... 250/251, 428, 461.2; 356/318, 338, 356/400; 382/128, 129
See application file for complete search history.

(56) References Cited

U.S. PATENT DOCUMENTS

| 4,573,796 A | * | 3/1986 | Martin et al. | 356/318 |
| 4,596,036 A | * | 6/1986 | Norgren et al. | 382/129 |
| 6,563,583 B2 | * | 5/2003 | Ortyn et al. | 356/400 |

(Continued)

OTHER PUBLICATIONS

Lloyd M. Davis, Jennifer L. Lubbeck, Kevin M. Dean, Amy E. Palmer and Ralph Jimenez; Microfluidic Cell Sorter for use in Developing Red Fluorescent Proteins with Improved Photostability; Year of Publication: 2013; Published in: Lab on a Chip; DOI: 10.1039/C3LC50191D; US.

(Continued)

*Primary Examiner* — David A Vanore
(74) *Attorney, Agent, or Firm* — Brownstein Hyatt Farber Schreck, LLP (57) ABSTRACT Devices and methods for screening emissive properties of a cell, such as the resistance to photobleaching or other photophysical property. In one example, a device may include a microfluidic reservoir having at least an input channel for receiving the cell, a main channel fluidly coupled with the input channel, at least a first output channel and a second output channel, the first and second output channels fluidly coupled with the main channel; and a multibeam interrogation section generating a plurality of light beams impinging upon the main channel of the microfluidic reservoir. As a cell passes from the input channel through the main channel of the microfluidic reservoir, the cell is exposed to the plurality of light beams thereby generating emissions that are received by a signal processing section. A cell trapping section selectively diverts the cell to the second output channel if the cell contains desired emissive properties.

20 Claims, 5 Drawing Sheets

(56) References Cited

U.S. PATENT DOCUMENTS

| | | | |
|---|---|---|---|
| 6,707,551 B2* | 3/2004 | Ortyn et al. | 356/338 |
| 6,944,322 B2* | 9/2005 | Johnson et al. | 382/128 |
| 7,824,065 B2* | 11/2010 | Maxik | 362/234 |
| 2012/0122084 A1* | 5/2012 | Wagner et al. | 435/6.1 |
| 2012/0202278 A1* | 8/2012 | Wagner et al. | 435/288.7 |
| 2012/0241643 A1* | 9/2012 | Palmer et al. | 250/428 |
| 2012/0244610 A1* | 9/2012 | Durack et al. | 435/288.7 |
| 2012/0307244 A1* | 12/2012 | Sharpe et al. | 356/338 |

OTHER PUBLICATIONS

Jennifer L. Lubbeck, Kevin M. Dean, Hairong MA, Amy E. Palmer and Ralph Jimenez; Microfluidic Flow Cytometer for Quantifying Photobleaching of Fluorescent Proteins in Cells; Year of Publication: 2012; Published In: Analytical Chemistry; DOI: 10.1021/ac202825z; US.

Jennifer L. Lubbeck, Kevin M. Dean, Lloyd M. Davis, Amy E. Palmer and Ralph Jimenez; Microfluidic Cytometer for Simultaneous High-Throughput Screening of Fluorescent Proteins on the Basis of Fluorescence Lifetime, Photostability, and Brightness; Year of Publication: 2012; Published In: Biophysical Journal; DOI: 10.1016/j.bpj.2011.11.1138; US.

Jennifer L. Lubbeck, Kevin M. Dean, Lloyd M. Davis, Amy E. Palmer and Ralph Jimenez; A Microfluidic Cell Sorter for Directed Evolution of Fluorescent Proteins Based on Dark-State Conversion and Photobleaching; Year of Publication: 2011; Published In: Biophysical Journal; DOI: 10.1016/j.bpj.2010.12.1176; US.

* cited by examiner

OPTICALLY INTEGRATED MICROFLUIDIC CYTOMETERS FOR HIGH THROUGHPUT SCREENING OF PHOTOPHYSICAL PROPERTIES OF CELLS OR PARTICLES

CROSS REFERENCE TO RELATED APPLICATION

This application claims the benefit of U.S. Provisional Patent Application No. 61/437,562 filed Jan. 28, 2011, entitled "Optically Integrated Microfluidic Cytometers For High Throughput Screening Of Photophysical Properties Of Cells Or Particles," the disclosure of which is hereby incorporated by reference in its entirety.

GOVERNMENT LICENSE RIGHTS

This invention was made with government support under grant number GM083849 awarded by the National Institutes of Health. The government has certain rights in the invention.

FIELD

This invention relates in general to flow cytometers or related devices.

BACKGROUND

Flow cytometry is a high-throughput measurement method for examining fluorescence in cells or particles or other items. However, as recognized by the present inventors, typically flow cytometers only screen cells on the basis of fluorescence intensity and cannot be used to examine the photobleaching of fluorescent proteins in cells, and conventional flow cytometers cannot typically be used to perform time-resolved and repeated measurements of fluorescent particles or cells.

Moreover, fluorescence photobleaching is a complex phenomenon that depends on several experimental and environmental factors. In fluorescent proteins, photobleaching occurs by both reversible and irreversible pathways, both of which may limit photon output of the fluorescent proteins. For instance, under single-molecule excitation conditions, fluorescent proteins emit 10-100× fewer photons than small-molecule fluorophores.

Fluorescent proteins (FPs) have revolutionized cellular imaging, however, they have a tendency to convert to non-radiative dark states and to undergo rapid, irreversible photobleaching. These effects limit their use in imaging applications involving low concentrations or long observation times.

SUMMARY

In light of the above and according to one broad aspect of an embodiment of the present invention, disclosed herein is a device for screening emissive properties of a collection or plurality of cells or particles, such as the resistance to photobleaching, photo-switching or other photophysical properties. In one example, the device may include a microfluidic reservoir having at least an input channel for receiving the cell, a main channel fluidly coupled with the input channel, at least a first output channel and a second output channel, the first and second output channels fluidly coupled with the main channel; and a multibeam interrogation section generating a plurality of light beams impinging upon the main channel of the microfluidic reservoir. As a cell passes from the input channel through the main channel of the microfluidic reservoir, the cell is exposed to the plurality of light beams thereby generating a plurality of emissions.

In one example, the device may also include a signal processing section for receiving the emissions of the cell after the cell has been exposed to each of the plurality of light beams, wherein the signal processing section is adapted to be connected with a computing device for analysis of the emissions. In another example, the device may include a cell trapping section for selectively diverting the cell to the second output channel if the computing device determines that the cell contains one or more desired emissive properties. The cell trapping section may include a laser generating a laser beam, and optics for selectively directing the laser beam within the microfluidic reservoir to a location that is adapted to divert the cell to the second output channel.

In another embodiment, the microfluidic reservoir can include an input for a suspension solution. The multibeam interrogation section may include a laser generating a laser beam, and optics for dividing the laser beam into the plurality of light beams. The plurality of light beams may be spaced apart in substantially equal amounts, and may be of substantially the same wavelength and of substantially the same intensity.

According to another broad aspect of another embodiment of the present invention, disclosed herein is a process for sorting particles based upon emissive properties, such as resistance to photobleaching or other photophysical property. In one example of the invention, the method may include providing a microfluidic reservoir having at least an input channel for receiving the particle, a main channel fluidly coupled with the input channel, at least a first output channel and a second output channel, the first and second output channels fluidly coupled with the main channel; introducing the particle into the input channel of the microfluidic reservoir; as the particle moves into the main channel, impinging the particle with a first light beam; measuring a first emissive property of the particle generated in response to the first light beam; impinging the particle with a second light beam; measuring a second emissive property of the particle generated in response to the second light beam; and determining whether the particle satisfies a desired criteria by at least comparing the second emissive property to the first emissive property.

In one example, the first and second light beams may be generated by a laser, and may be of substantially the same wavelength and may also be of substantially the same intensity.

In another embodiment, the method may also include that if the particle satisfies the desired criteria, the particle is diverted into the second output channel of the microfluidic reservoir. In another example, the method may include if the determining operation determines that the particle does not satisfy the desired criteria, then allowing the particle to travel into the first output channel of the microfluidic reservoir. The diverting operation may include selectively impinging an infrared laser beam onto the particle to impart a force upon it.

In another example, the method may include impinging the particle with a third light beam; measuring a third emissive property of the particle generated in response to the third light beam; and determining whether the particle satisfies a desired criteria by at least comparing the first, second and third emissive properties. The first, second and third light beams may be substantially equally spaced apart.

It is understood for the various embodiments described herein, that depending upon the particular implementation, the first and second channels can be interchanged (or the diverting operation can be altered) so that cells or particles that do not satisfy a desired criteria can be diverted, if desired.

The features, utilities and advantages of the various embodiments of the invention will be apparent from the following more particular description of embodiments of the invention as illustrated in the accompanying drawings.

DETAILED DESCRIPTION

Figure 1:
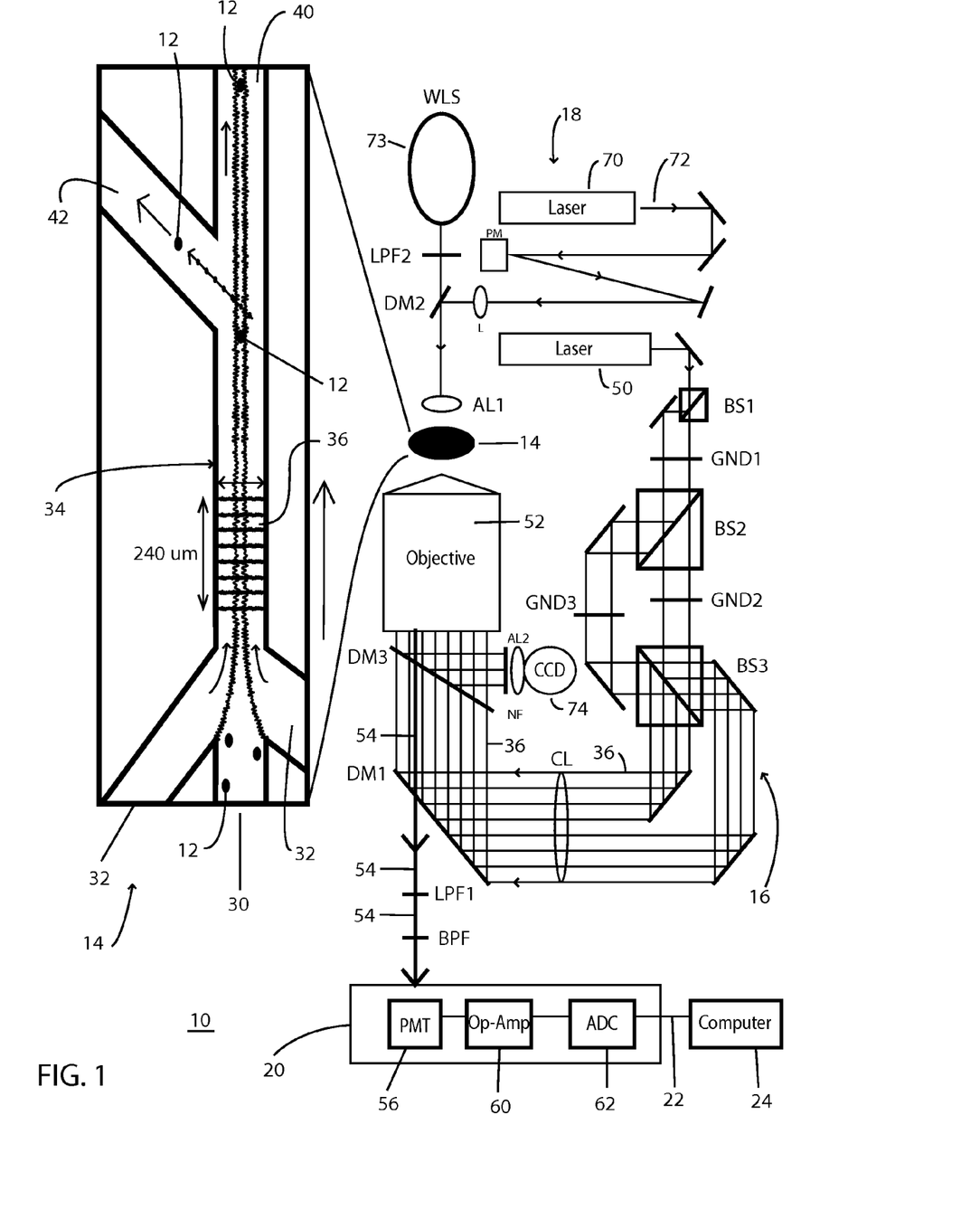
FIG. 1 illustrates an example of a system and devices for an optically integrated microfluidic cytometer device, in accordance with an embodiment of the present invention.
Figure 2:
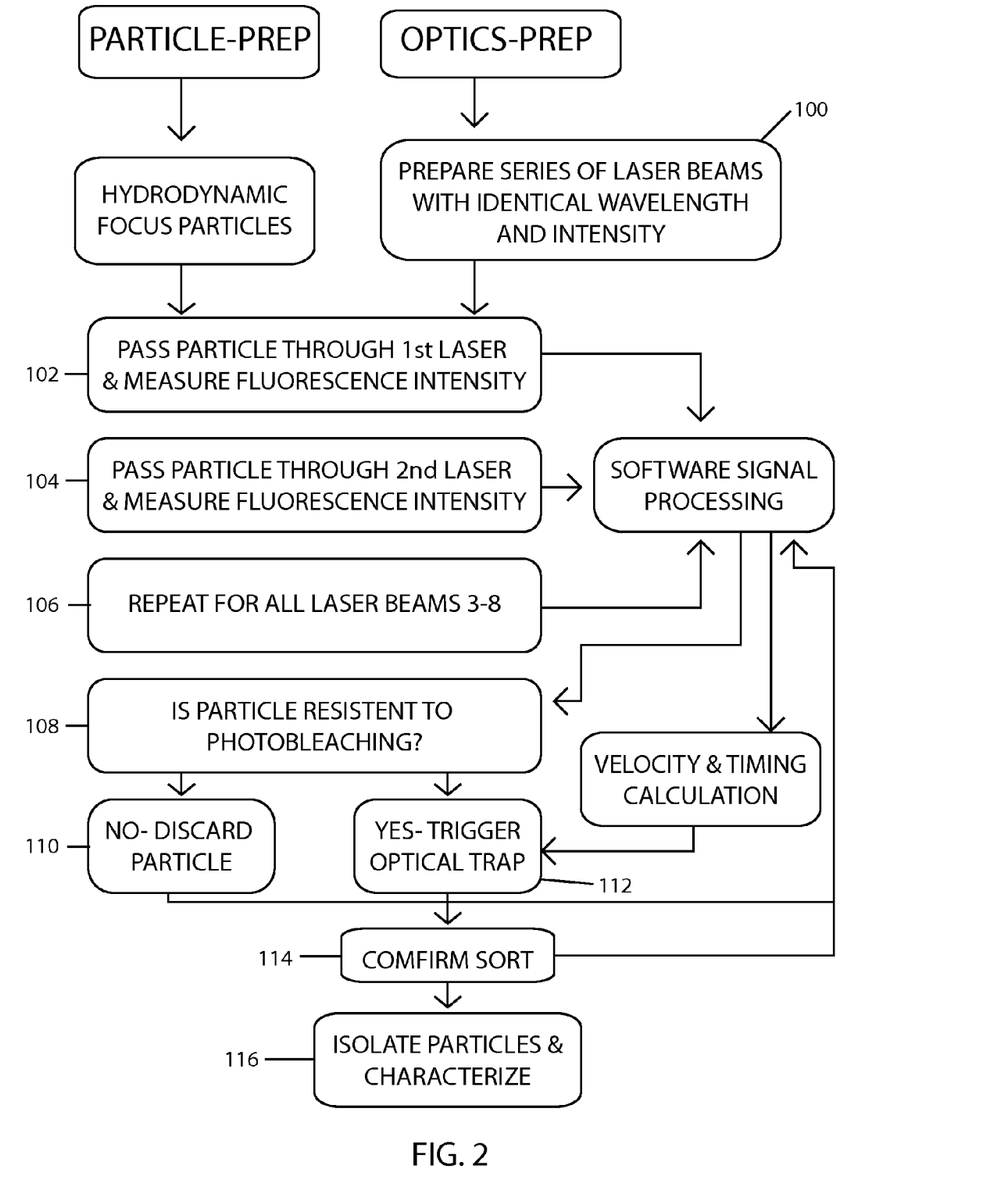
FIG. 2 illustrates an example of operations for screening of photophysical properties of cells or particles, in accordance with one embodiment of the present invention.
Figure 3:
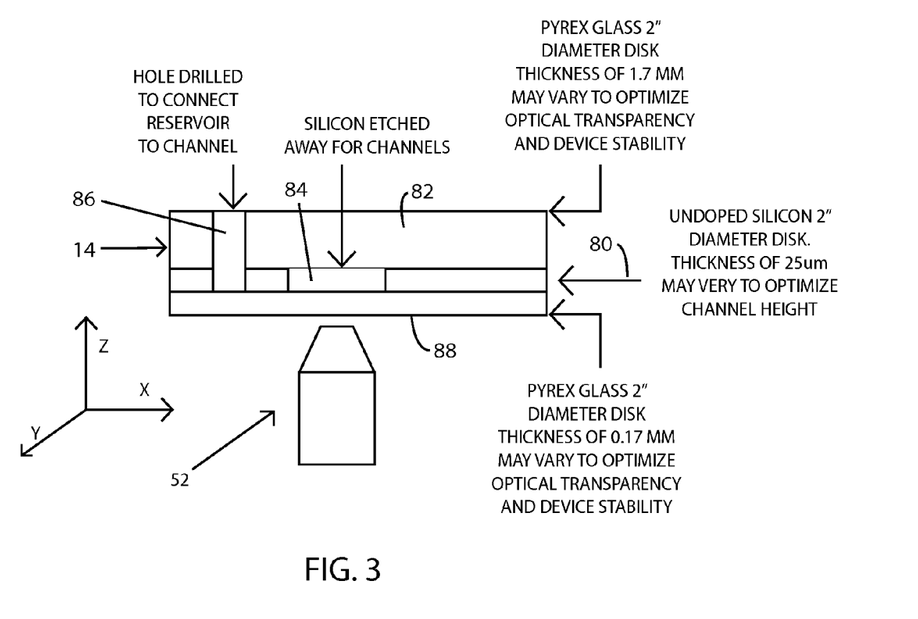
FIG. 3 illustrates a cross-sectional view of an example of a microfluidic sample reservoir, in accordance with one embodiment of the present invention.

As shown in FIGS. 1-3 disclosed herein are various embodiments of a versatile microfluidic device 10, and associated methods, capable of measuring or screening photobleaching or other photophysical properties on individual cells or particles or other items 12, such as mammalian cells, at high-throughput rates (e.g., greater than rates of 20 cells per second if desired).

Embodiments of the present invention can be used for analyzing photophysical properties in particles, cells, fluorescent particles, fluorescent proteins, fluorescent dyes including small-molecule dyes, plasmonic nano crystals, fluorescent protein carriers, small molecule fluorophores (i.e., fluoroscien, rhodamine, cy3, cy5), or any other cell, molecule, droplets or particle 12. For simplicity of this description, these items are interchangeably referred to herein as sample cells, particles, or fluorescent proteins, as the items 12 being analyzed by embodiments of the present invention. It is understood that the terms cell(s), particle(s) or fluorescent protein(s) are intended to include all items 12 that could be analyzed by embodiments of the present invention.

Embodiments of the invention can be used for various purposes described herein, including to investigate and analyze the photophysics for diverse fluorescent protein sequences. By employing a series of spatially separated excitation beams (e.g., laser beams) in a cytometer 10 as described herein, the irreversible component of photobleaching can be isolated. For instance, a mixture of red fluorescent proteins was assayed, and mCherry was identified as the variant with the lowest degree of irreversible photobleaching.

Embodiments of the invention can be used to complement existing methods for fluorescent protein analysis, and thereby may facilitate development of next-generation fluorescent proteins for single-molecule research or development of other cells, particles, molecules, or items 12.

Moreover, embodiments of the invention can be used to screen the photobleaching of cells 12 at high rates, and can be used for example to examine large numbers of genetic variants in cells 12. Embodiments of the invention can be used with genetic libraries of fluorescent proteins to identify, select and enable directed evolution of improved and new proteins, fluorescent dyes, or other items with superior photostability for biological imaging.

Embodiments of the present invention can also make multiple measurements on cells 12 (or particles or other input samples) over time as the cells 12 are flowing, and cells 12 that have specific responses to such measurements can be selected out for further interrogation.

FIG. 1 illustrates an example of an optically integrated microfluidic cytometer device 10, and associated system, in accordance with an embodiment of the present invention.

In one example of the invention, a cytometer device 10 includes a microfluidic sample reservoir 14; a multi-beam laser interrogation section 16; a cell trapping section 18; and a signal processing section 20. The signal output 22 of the device may be connected with a computer 24 having analysis software, such as LabView, operating thereon.

The microfluidic sample reservoir 14 is provided to receive a plurality of cells, particles, or other sample materials 12, which will be analyzed by the device 10. Portions of the microfluidic sample reservoir 14 are shown, in exploded view, in FIG. 1, and in cross-section in FIG. 3.

In one example, the microfluidic sample reservoir 14 has an input channel 30 for receiving the sample 12 to be analyzed, and suspension solution input channels 32 may also be provided to receive solution that is used to contain and guide sample cells 12 through the reservoir 14. Channel 32 can also be used to deliver chemical reagents, which can be useful for perturbing the environment around cells 12 and/or measuring time-dependent fluorescent changes that occur in the main channel 34. The input channel 30 and solution input channels 32 flow into a main channel 34, where the interrogation of sample cells 12 occurs by operation of the multiple light beams 36 produced by the multi-beam laser section 16. In the example shown in FIG. 1, eight beams of light 36 of the same wavelength and similar intensity are generated by the multi-beam laser section 16 (described below), and each sample cell 12 passes through the series of light beams 36, as shown in FIG. 1. The sample reservoir 14 also includes at least two output channels—a first output channel/path 40 where an undeflected sample cell 12 will travel when the cell trapping section 18 is not activated in one example; and a second output channel 42 is provided to receive an individual sample cell 12 that is deflected under the control of the cell trapping section 18, described below. In other embodiments, a plurality of output channels can be provided, so that sorting of cells/particles 12 can be based, for example, on the degree of the presence of a particular property into any number of output channels.

In this manner, a sample cell 12 is passed from the input 30 of the reservoir 14 through the multi-beam interrogation section 36 of the main channel 34, and, if certain characteristics are detected in the sample cell 12, in one embodiment of the invention the sample cell 12 is deflected into the second output channel (deflected path) 42, otherwise the sample cell 12 passes along to the first output channel 40 via the undeflected path.

In one example, the multi-beam laser interrogation section 16 is active during operation of the device 10, and may include a laser 50 (e.g., 532 nm laser providing to 2 W in power) whose output is split into multiple beams 36 (e.g., eight beams) by performing multiple passes through separate 50:50 beam splitters (e.g., shown as BS1, BS2, BS3) with a series of mirrors or reflectors. In one example, optical imperfections in the beam-splitters produce eight beams of approximately 9% intensity for each beam. Such imperfections may be corrected by using one or more neutral density filters, such as a series of gradient neutral density filters shown as GND1, GND2 and GND3 in FIG. 1. After splitting, the beams are shaped by a cylindrical lens (CL) and directed into an inverted microscope including a dichroic mirror (DM1) that directs the multiple beams 36 to an objective optic/lens 52 (e.g., 20×, 0.45 NA air-objective) which focuses the multiple beams 36 inside of the microfluidic channels 34 of the sample reservoir 14.

In another example, the microfluidic reservoir 14 can be provided with diffractive optics or masking that functions to split a laser beam into multiple interrogation beams 36 as the laser beam impinges on the reservoir 14. Such could be used in place of one or more of the optics shown in FIG. 1. Hence, the generation of multiple interrogation beams 36 can be generated external to the reservoir 14, or can be created on or within reservoir 14.

If desired, light beams of multiple different wavelengths could be employed to measure how the sample responds to or is modified by different excitation wavelengths, and/or the intensities could be varied to measure other photophysical properties such as photon output as a function of excitation intensity (i.e., excited state saturation). For example, a second laser (not shown) operating at a different wavelength could be used to generate one or more laser beams at a different wavelength/frequency than as produced by laser 50. Optics similar to those described herein could be used to direct the beams from the second laser into the objective 52 and into the main channel 34 of the reservoir 14. The beams from the second laser could be interspersed with beams from the first laser 50. Filters can be used to reduce spectral cross-talk between the laser beams. This enables measurement of various photopyhsical properties, including the photoswitching efficiency of the cell/particle/molecule. Photoswitchable molecules respond to different wavelengths—one wavelength induces fluorescence, while other wavelengths induce transitions into or out of a dark state (while causing no emission/response). Photoswitchable molecules have become important in recent years for their use in sub-diffraction imaging. The measurement is by a similar process of comparing the response at a plurality of laser beams as described herein, but at least one intervening beam is of a different color/wavelength.

Embodiments of the present invention may utilize a range of excitation intensities (e.g., 0.1 kW/cm$^2$ to GW/cm$^2$), depending upon the particular implementation.

The resulting fluorescence emission 54 generated in response to the multi-beam interrogation laser 50, by the sample cell 12 (which is generally at different wavelengths than the excitation laser) is collected through the same or different objective optic 52 and separated from the excitation light 36 by, for example, a dichroic mirror (DM1), long-pass filter (LPF1) and a band-pass filter (BPF). Fluorescence emissions 54 from the sample cells 12 are typically at longer wavelengths than the excitation wavelengths of the multi-beam interrogation laser 50; therefore embodiments of the present invention can separate and capture the cell's photophysical emissive properties when compared to the excitation interrogation laser 50. Other photophysical properties such as vibrational types of spectroscopy (i.e., Raman) occur at wavelengths longer than (stokes) and wavelengths shorter than (anti-stokes) the excitation laser. If desired, these photophysical properties could also be measured.

Resulting emission intensity is detected by the signal processing section 20, which in one example includes a photomultiplier tube 56(PMT) that converts received light/photons 54 into an electrical signal 58, and may be configured to be red-optimized; operational amplifiers 60 (i.e., AC coupled transimpedance op-amps) which improve the signal to noise ratio by filtering out high and low frequency noise components; and an analog to digital converter 62 to create digital signals 22 that can be coupled with a computer 24 for further analysis. The analysis may include analysis of the photophysical properties of the emissions 54 from the cells, including but not limited to fluorescence intensity (brightness), photostability, photo-switching, resistance to photobleaching and reversible dark state conversion, among others. This analysis can occur in real-time, if desired, as the cell 12 is moving within the reservoir 14.

In one example, the cell trapping section 18 is activated only when certain photophysical characteristics are detected in a sample cell 12, so that the sample cell 12 is diverted to the second output channel 42 (or conversely if desired, the device 10 could be configured so that cell trapping occurs if certain characteristics are absent in the sample cell). The cell trapping section 18 uses optical forces from a light source 70 to trap, redirect or sort sample cells 12.

The cell trapping section, in one example, may include a laser 70 (e.g., 20 W 1064 nm Yttrium fiber IR laser) directed through a lens assembly (LA) and mirrors/reflectors onto a piezoelectric mirror (PM) for rapid lateral steering of the laser beam 72. The laser beam 72 is then directed through a lens (L), reflected off of a dichroic mirror (DM2) and focused inside of the microfluidic sample reservoir with an aspheric lens (AL1). This laser beam 72 can be digitally modulated at a rate sufficient to provide precision triggering and limited exposure of the cell 12 to laser light 72. In one example, the trapping laser 70 is modulated at around 20 KHZ. The rate may be selected based on factors such as but not limited to the cell flow speed (i.e., 100 to 1000 times the particle flow rate), how long the cells 12 should stay in the laser beams 36 to be bleached (i.e. extent of photo destruction) and how much optical force is available to deflect during sorting.

Any laser (or light source) 70 can be used for optical trapping or re-direction by optical force, in the cell trapping section 18. However, it is believed that infrared (IR) light produces lower amounts of damage/stress to cells 12 and generally does not affect the fluorophores. The wavelength of the trapping light source 70 can be selected to avoid heating the suspension solutions (which may contain water) and/or damaging the cells 12.

Other methods of cell sorting can be used, such as pneumatic (pressure) methods, dielectrophoretic methods, thermal methods, fluidic methods, or any conventional sorting technique, if desired.

In one example, the computer 24 is coupled directly or indirectly with the cell trapping section 18, and sends a control signal to activate the cell trapping section 18 upon determination that the cell or particle 12 under test satisfies certain one or more criteria.

Quality control of the operation of the device—including visually monitoring of fluid flow, trap efficiency, optical alignment, clogging, burning caused by the lasers, hydrodynamic focal width, cell adhesion to the sides of the channels—may be provided, along with monitoring of simultaneous wide field imaging, optical trapping, and detection of fluorescence,—through the use of a white light source 73 (WLS), a long pass filter (LPF2), dichroic mirror (DM3), an aspheric lens (AL2), a notch filter (NF), and a CMOS camera 74 (CCD). An operator of the device 10 can watch the CCD camera 74 during use of the device, or images or video from the CCD camera 74 can be recorded and/or stored in digital form if desired.

In FIG. 3, a cross-section of a sample reservoir 14 is shown, and the reservoir 14 may be formed to include the fluid channels shown in FIG. 1. In one example, the sample reservoir is constructed by anodically bonding a circular, 2"-diameter, polished, undoped silicon wafer 80 (channel layer) to a circular 2"-diameter piece of Pyrex 82 (base layer). The Pyrex base layer 82 is sufficiently thick to provide a stable platform, and may be between approximately 0.13 mm to 1.7 mm thick or more. The silicon wafer's 80 thickness may vary as it is subsequently polished to a thickness of 25 micrometers in one example. Once polishing is complete, areas 84 of the silicon are etched away using for example an SF-6 plasma etcher and standard lithography techniques. Holes 86 such as 1 mm holes may be drilled at the ends of each channel through the glass-silicon unit. The reservoir may be anodically bonded to another circular, 2"-diameter Pyrex disk to form a top layer 88 which is 1.7 mm—1.7 micrometers thick in one example.

A mask used for the lithography may be selected such that the channel widths are between 100-400 micrometers, and are of the order of 0.5 mm-1 cm in length. The thickness of the silicon layer 80 constrains the depth of the channels to 25 micrometers, in one example. As shown in FIG. 1, the reservoir may include three input channels 30, 32 and two output channels 40, 42 linked by a main channel 34. The main channel 34 defines the multi-beam interrogation region. One or more outermost input channels 32 may be used for a sheath fluid or suspension solution of choice, which serve to hydrodynamically focus the sample cells 12 in the center input channel 30. Multiple output channels 40, 42 are used for separating the sample cells 12, or sorting them. The input and output channels may be in fluidic connection to on-chip reservoirs. The sample and sheath fluids may be inserted into the input sample and sheath fluid reservoirs, which in one example may be approximately 200 micro liters or less or more if desired, such as 20 to 500 micro liters. The output channels can empty into separate on-chip reservoirs such that the sample cells can be recovered after sorting.

To house the sample reservoir, the microfluidic portions in one example are sandwiched between a base plate with a large hole in the middle, which allows for visualization of the microfluidic channel and interrogation region, and another rigid piece used to hold the reservoirs. Reservoirs to hold the sample and sheath fluids may be formed by drilling holes or cavities in a hydrophobic plastic. This plastic piece press fits to the microfluidic using "O"-rings to form a watertight seal between the hydrophobic plastic and the input channels, such that the reservoirs formed in the plastic are in fluidic connection with the input channels. The reservoirs are subsequently pressurized to force the fluids through the microfluidic channels.

It is important to note that a sample reservoir and portions thereof may be made out of other materials and/or using other techniques. Undoped silicon and glass are used in one example of the invention to avoid interaction with stray laser light. In other examples, the sample reservoir may be made using all glass, PDMS and glass, or doped silicon and glass, for example. However, the latter two options may be problematic when working with high-intensity laser light or an optical setup with many stray beams, as they are less optically transparent and might burn.

Figure 4:
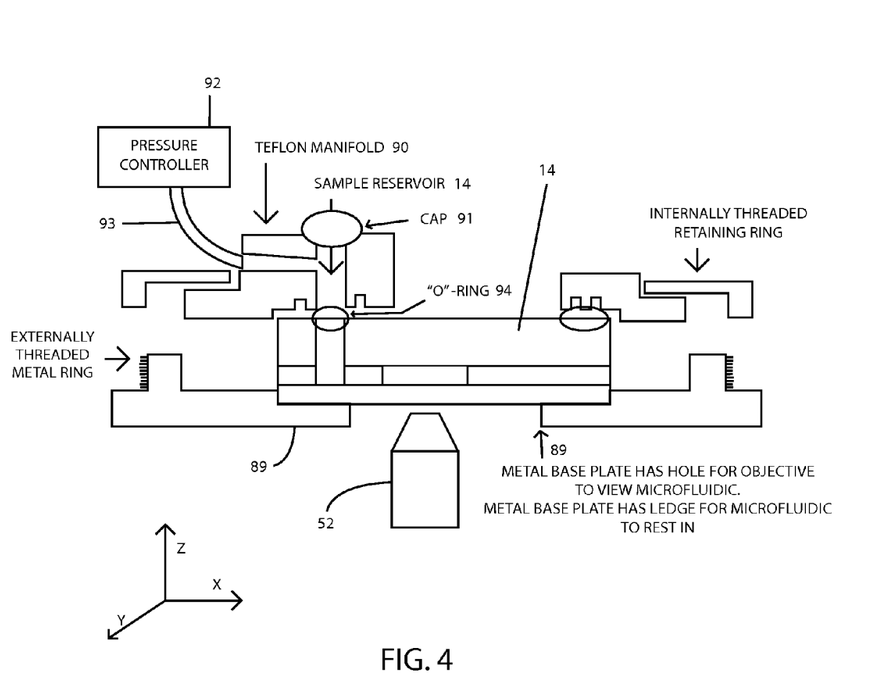
FIG. 4 illustrates a sectional view of an example of device 10, including reservoir 14, in accordance with an embodiment of the present invention.

As shown in FIG. 4, optic 52 is positioned to impart the interrogation beams 36 into (and receives emissions 54 out from) the reservoir 14.

Figure 5:
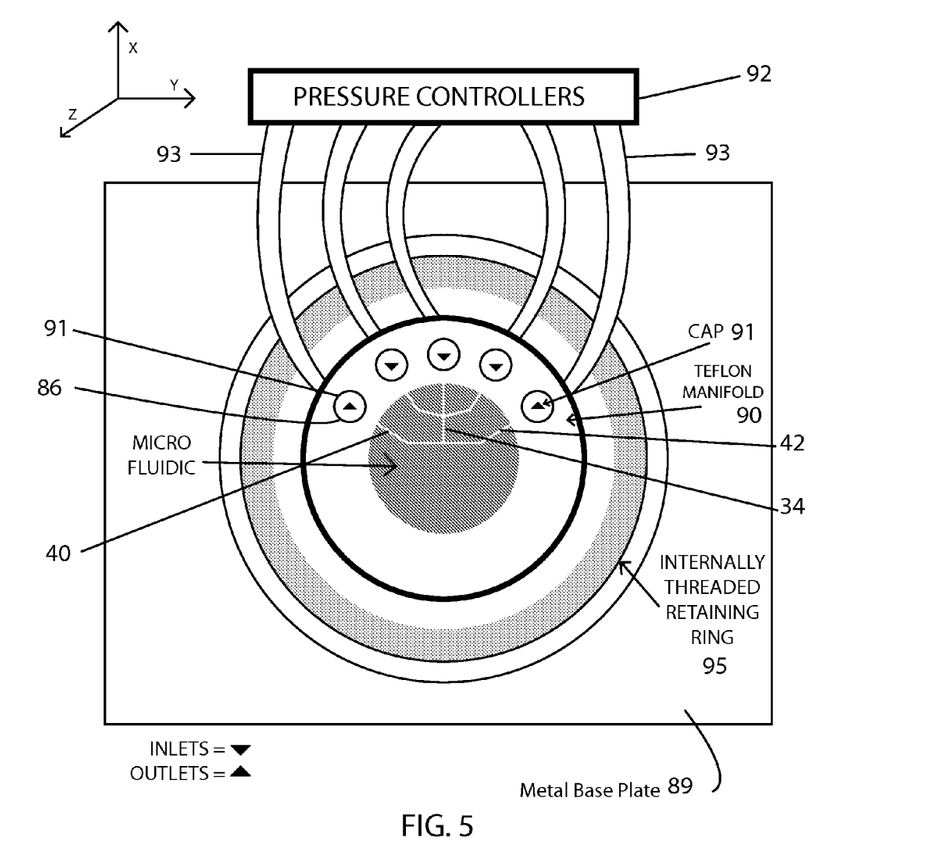
FIG. 5 illustrates a top view of FIG. 4, in accordance with an embodiment of the present invention.

While many configurations of reservoir 14 are possible, FIGS. 4-5 show one example. The reservoir structure 14 can sandwiched between a metal base 89 and a retaining ring 95. A manifold 90 can be used to provide multiple fluid storage reservoirs (i.e., to hold samples or other fluids or droplets, or store the outputs), and the manifold 90 can be coupled with a pressure controller 92 through tubes 93. O-rings 94 can be used between the manifolds 90 around each opening/channel 86 and layer 82. A cap 91 can be used to enclose each reservoir opening/channel 86. As shown in the top view of FIG. 5, three input channels are shown and two output channels are shown, in this example.

FIG. 2 illustrates an example of operations for screening of photophysical properties of cells or particles 12, in accordance with one embodiment of the present invention.

The sample cells/particles 12 may be prepared by rinsing and filtering them for size, and they can be suspended in a density matched solution that is preferably optically clear and pH-buffered. The solution preferably does not significantly interfere with the signal or the noise of the detected fluorescence 54 which will be emitted by the sample cells 12. Density matching provides a buoyant force for the cells/particles which prevents aggregation of the cells/particles, and allows more consistent flow-rates as the sample cells 12 flow through the device 10. Cells/Particles 12 are then placed into the on-chip input sample reservoir and an optically clear and pH-buffered sheath fluid is placed in the input sheath reservoirs for downstream hydrodynamic focusing of the cells/particles 12.

In one example, input pressures can be controlled for the input sample reservoir and the two input sheath channels 32, allowing operating velocity of the cell/particle and focusing width of the sample fluid to be controlled.

In one example, at operation 100, a series of multiple (e.g., 8) laser beams 36 are created, preferably with identical wavelengths and similar laser intensity (although different wavelengths and intensities could be used if desired). Laser alignment within the microfluidic sample reservoir, and relative to the flow of the cells/particles, can be confirmed. Alignment of the infrared laser beam 72 of the cell trapping section 18 may also be confirmed and operating powers of the lasers set.

In one example, to screen photophysical properties of cells or particles 12, optical measurements are performed at operations 102-108. At operation 102, particles 12 are passed through the first of a series of laser beams, which in one example are line-shaped or elliptically shaped. At operations 104-106, as the sample cells/particles 12 travel sequentially through the multiple line shaped and intensity matched excitation laser beams 36, each line shaped beam causes photonic excitation 54 of the fluorescent cell/particle 12 of interest and induces photodamage that is apparent upon excitation by the subsequent excitation laser beam.

At operations 102-106, the fluorescence intensity of a sample cell/particle's response to an excitation laser beam 36 may be detected and measured using a photomultiplier tube (PMT) 56, which converts the emitted fluorescence photons into an electrical signal (e.g., current) that is proportional to photon flux. In one example, the electrical current undergoes analog electrical low-pass and high-pass filtering, to eliminate spurious noise in the signal and improve the signal to noise ratio. The resulting filtered current then undergoes conversion to a voltage signal that is digitized by an analog-to-digital converter, and received, analyzed and recorded on a computer or other device.

At operations 102-106 and 108, the fluorescence intensity of the Cell/Particle is measured for each excitation event (e.g., each pass of the sample particle/cell through a laser beam or line-shaped beam), and the photo-induced damage is determined quantitatively using software, such as LabView, by comparing the fluorescence intensity after excitation by each subsequent laser excitations line or beam 36.

At operation 108, photodamage is observed by a decrease in the fluorescence intensity in subsequent excitations (i.e., beam 2, beam 3, . . . beam n), and the cumulative damage can be determined in a high-throughput fashion by measuring the fluorescence intensity 54 of each beam relative to the first beam (operation 102).

Decision operation 108 determines if this sample cell/particle 12 is photostable and resistant to photobleaching.

In one example, desirable properties of a sample cell/particle may be established by a user-input threshold (i.e., 50% of initial fluorescence intensity) into software, thereby indicating if a sample cell/particle 12 contains the desirable properties based upon the optical measurements taken at operations 102-106. This threshold can be used by decision operation 108.

In one example, operation 108 may include determining if the fluorescence intensity 54 of the sample cell 12 in response to the last beam (e.g., beam 8) is identical or substantially identical to the initial fluorescence intensity response 54 of the sample cell 12 measured in response to beam 1 at operation 102; if so, then photodamage is not occurring indicating that this sample cell/particle 12 is photostable and resistant to photobleaching, and control may be passed to operation 112 where the sample cell/particle 12 may be trapped (i.e., by enabling the laser 70 of the cell trapping section 18) and retained for further analysis or characterization.

If however, operation 108 determines that the sample cell/particle 12 is not resistant to photobleaching, then control is passed to operation 110 where the sample cell/particle 12 may be discarded. In one example, operation 108 may include determining if the fluorescence intensity response 54 of the sample cell/particle 12 to beam 8 is significantly less than the fluorescence intensity response 54 of the sample cell/particle 12 measured from beam 1; if so, then a significant amount of photon-induced damage has occurred and the cell/particle 12 is not photostable.

In one example, if the sample cell/particle 12 does not exhibit the desired photophysical properties, at operation 110 the optical trap 18 is not triggered and the cell 12 continues to travel into the 'discard' output (i.e., 40) in the microfluidic device 10. A percentage of cell/particles that do not meet the desired criteria of photophysical properties may be calculated and maintained for offline statistical analysis if desired.

In one example, the multiple laser beams 36 of operation 100 are aligned at a set and known distance, and thus, by calculating the time it takes to travel from the first beam to the last beam (e.g., beam 1 to beam 8), the velocity of the cell/particle 12 as it travels through the reservoir can be determined. This information can be used for triggering and timing of the optical trap 18.

In one example, if the sample cell/particle 12 exhibits the desired photophysical properties, at operation 112 the optical trap 18 is triggered using timing data generated from the cell velocity, and the sample cell 12 is then optically diverted or sorted using photonic forces imparted by the infrared laser 70 of the cell trapping section 18. A percentage of cell/particles that meet the desired criteria for photophysical properties may be calculated and maintained by software for offline statistical analysis, if desired.

Alternatively, if desired, operations 110-112 could be changed so that particles 12 that satisfy the test of operation 108 are not redirected while particles 12 that do not satisfy the test of operation 108 are redirected/trapped.

At operation 114, if desired, success of optical sorting can be confirmed quantitatively by measuring the fluorescence 54 of a cell/particle 12 that was selected and retained by operations 108, 112. In one example, if desired, an additional (e.g., ninth) light beam may be introduced in one of the output channels (i.e., 42) of the device 10 and impinged upon the trapped cell/particle to confirm that the cell/particle 12 has appropriately been sorted.

Upon sorting of the cells, at operation 116, the cells/particles 12 are isolated and spectroscopically interrogated to confirm the success of the sort and/or determine other characteristics regarding the sample cells/particles 12.

Hence, it can be seen that embodiments of the present invention provide the ability to identify various properties of cells or particles 12, or in other items as described above.

For instance, in one example, the interrogation beams 36 intersect a hydrodynamically focused stream in a microfluidic channel 34 to stroboscopically interrogate each cell 12. Subsequently, a piezo-steered infrared trapping beam 72 deflects cells 12 for sorting. The multi-beam sequence 36 provides millisecond timescales of excitation and dark intervals to separate the effects of dark-state conversion and irreversible photobleaching. Through the use of embodiments of the present invention, sorting of genetic libraries of cell-based FPs may be achieved on the basis of photokinetics, independent of FP expression level, and characterizing FP photophysics can be provided in order to aid in the engineering of a new generation of brighter more photostable FPs or photoswitchable FPs.

Improvements in the brightness and color of each fluorescent protein prior to the termination of fluorescence (photobleaching) can dramatically enhance biomedical fluorescence imaging capabilities. These advances can aide in monitoring of living cells over longer periods of time and can be used by scientists to follow populations of cells in whole animals. Such advances can be useful in various ways, such as but not limited to studies of basic cell biology, imaging the progression of cancer, monitoring bacterial infections, and in the development of assays and screens for drug discovery.

In one example, embodiments of the present invention can be used to form microfluidic cytometers for high-throughput sorting of FP-expressing mammalian cells based on the selective measurement of photostability, magnitude of dark-state conversation, or the combined effects of both.

While embodiments of the invention have been described in terms of a configuration to provide a specific type of physical measurement (photobleaching and dark state conversion), it is understood that embodiments of the invention may be configured to measure different parameters. For instance, embodiments of the invention may be adapted to serve as quality control for why different cells, beads, bacteria, particles or fluorophores have different properties (i.e., define and understand sample heterogeneity). Embodiments of the invention may be used in high throughput screens or assays for making better fluorophores; for exploring how cells respond to light/irradiation; or following events in cells over time (response of cells to drugs, for example).

It is understood that the specific dimensions disclosed herein are provided as examples, and that embodiments of the present invention may be formed using other sizes or dimensions of the components without departing from the teachings herein.

While the methods disclosed herein have been described and shown with reference to particular operations performed in a particular order, it will be understood that these operations may be combined, sub-divided, or re-ordered to form equivalent methods without departing from the teachings of the present invention. Accordingly, unless specifically indicated herein, the order and grouping of the operations are not a limitation of the present invention.

It should be appreciated that reference throughout this specification to "one embodiment" or "an embodiment" or "one example" or "an example" means that a particular feature, structure or characteristic described in connection with the embodiment may be included, if desired, in at least one embodiment of the present invention. Therefore, it should be appreciated that two or more references to "an embodiment" or "one embodiment" or "an alternative embodiment" or "one example" or "an example" in various portions of this specification are not necessarily all referring to the same embodiment.

It should be appreciated that in the foregoing description of exemplary embodiments of the invention, various features of the invention are sometimes grouped together in a single embodiment, figure, or description thereof for the purpose of streamlining the disclosure and aiding in the understanding of one or more of the various inventive aspects. Inventive aspects lie in less than all features of a single foregoing disclosed embodiment, and each embodiment described herein may contain more than one inventive feature.

While the invention has been particularly shown and described with reference to embodiments thereof, it will be understood by those skilled in the art that various other changes in the form and details may be made without departing from the spirit and scope of the invention.

The invention claimed is:

1. A device for screening emissive properties of a cell, comprising:
   a microfluidic reservoir having at least an input channel for receiving the cell, a main channel fluidly coupled with the input channel, and at least a first output channel and a second output channel, the first and second output channels fluidly coupled with the main channel; and
   a multibeam interrogation section generating a plurality of light beams impinging upon the main channel of the microfluidic reservoir;
   so that as a cell passes from the input channel through the main channel of the microfluidic reservoir, the cell is exposed to the plurality of light beams thereby generating a plurality of emissions.

2. The device of claim 1, further comprising:
   a signal processing section for receiving the plurality of emissions of the cell after the cell has been exposed to each of the plurality of light beams, wherein the signal processing section is adapted to be connected with a computing device for analysis of the plurality of emissions.

3. The device of claim 2, further comprising:
   a cell trapping section for selectively diverting the cell to the second output channel if the computing device determines that the cell contains one or more desired emissive properties.

4. The device of claim 3, wherein the cell trapping section includes a laser generating a laser beam, and optics for selectively directing the laser beam within the microfluidic reservoir to a location that is adapted to divert the cell to the second output channel.

5. The device of claim 1, wherein the emissive properties of a cell include resistance to photobleaching.

6. The device of claim 1, wherein the microfluidic reservoir includes an input for a suspension solution.

7. The device of claim 1, wherein the multibeam interrogation section includes a laser generating a laser beam, and optics for dividing the laser beam into the plurality of light beams.

8. The device of claim 1, wherein the plurality of light beams of the multibeam interrogation section are spaced apart in substantially equal amounts.

9. The device of claim 1, wherein the plurality of light beams of the multibeam interrogation section are of substantially the same wavelength.

10. The device of claim 1, wherein the plurality of light beams of the multibeam interrogation section are of substantially the same intensity.

11. A process for sorting particles based upon emissive properties, comprising:
    providing a microfluidic reservoir having at least an input channel for receiving the particle, a main channel fluidly coupled with the input channel, and at least a first output channel and a second output channel, the first and second output channels fluidly coupled with the main channel;
    introducing the particle into the input channel of the microfluidic reservoir;
    as the particle moves into the main channel, impinging the particle with a first light beam;
    measuring a first emissive property of the particle generated in response to the first light beam;
    impinging the particle with a second light beam;
    measuring a second emissive property of the particle generated in response to the second light beam; and
    determining whether the particle satisfies a desired criteria by at least comparing the second emissive property to the first emissive property.

12. The method of claim 11, further comprising:
    if the determining operation determines that the particle satisfies the desired criteria, diverting the particle into the second output channel of the microfluidic reservoir.

13. The method of claim 12, wherein the diverting operation includes selectively impinging an infrared laser beam onto the particle.

14. The method of claim 11, further comprising:
    if the determining operation determines that the particle does not satisfy the desired criteria, then allowing the particle to travel into the first output channel of the microfluidic reservoir.

15. The method of claim 11, further comprising:
    impinging the particle with a third light beam;
    measuring a third emissive property of the particle generated in response to the third light beam; and
    determining whether the particle satisfies a desired criteria by at least comparing the first, second and third emissive properties.

16. The method of claim 15, wherein the first, second and third light beams are substantially equally spaced apart.

17. The method of claim 11, wherein the emissive properties of a particle include resistance to photobleaching.

18. The method of claim 11, wherein the first and second light beams are of substantially the same wavelength.

19. The method of claim 11, wherein the first and second light beams are of substantially the same intensity.

20. The method of claim 11, wherein the first and second light beams are generated by a laser.

* * * * *